United States Patent [19]
De Somma

[11] Patent Number: 6,069,293
[45] Date of Patent: May 30, 2000

[54] HEALING PACK AND APPLICATOR AND METHOD

[76] Inventor: Carmine R. De Somma, 1155 Las Dalias Ct., Turlock, Calif. 95380

[21] Appl. No.: 09/186,387

[22] Filed: Nov. 5, 1998

[51] Int. Cl.[7] .............................. A61F 13/00; A61F 15/00; A61K 7/16
[52] U.S. Cl. ................................ 602/48; 602/42; 602/43; 602/54; 602/57; 424/49
[58] Field of Search ................................... 424/49, 53, 54, 424/709; 602/79, 41–59; 128/888, 889

[56] References Cited

U.S. PATENT DOCUMENTS

| | | | |
|---|---|---|---|
| 4,183,914 | 1/1980 | Gaffar et al. | 424/48 |
| 4,244,698 | 1/1981 | King et al. | 424/54 |
| 5,898,037 | 4/1999 | Marx | 424/49 |

*Primary Examiner*—Kim M. Lee
*Attorney, Agent, or Firm*—Linval B. Castle

[57] ABSTRACT

A healing pack for applying an epsom salts soak to body parts normally inaccessible to soaking includes a pliable, saucer shaped, foam cup containing a water soluble gel mixture of epsom salts and glycerin. When applied to sprains and contusions it functions the same as soaking in epsom salts and water.

6 Claims, 1 Drawing Sheet

HEALING PACK AND APPLICATOR AND METHOD

This invention relates to the medical healing agent for certain types of bruises and to the applicator for applying it.

SUMMARY OF THE INVENTION

It is well known that minor traumas, such as ankle sprains and elbow or hand injuries, can be relieved and swelling reduced by soaking the injured area in a solution of epsom salts and water. But to treat other injured body parts, for example a shoulder or hip, soaking can be very difficult.

Swelling following a minor injury to a hip, shoulder or other body part inaccessible to epsom salts soaking can easily be treated by replacing the water with glycerin in the epsom salts solution to produce a gel-like substance. This gel is applied to the applicator of the invention which is applied over the injured site to accomplish the same function as a soak.

The applicator is formed of a molded foam sheet, preferably circular and ⅛ inch thick with ⅛ inch high side walls topped with an adhesive. The gel is applied into the interior and covered with a thin sheet covering of Teflon®. When an injury occurs that is not an open wound, burn, abrasion or fungal infection, the Teflon® covering is peeled off and the exposed epsom salts/glycerin gel healing pack is held in place over he swollen area with tape, roller dressing, or Velcro®.

BRIEF DESCRIPTION OF THE DRAWINGS

In the drawings that illustrate preferred embodiments of the invention.

DETAILED DESCRIPTION

Figure 1:
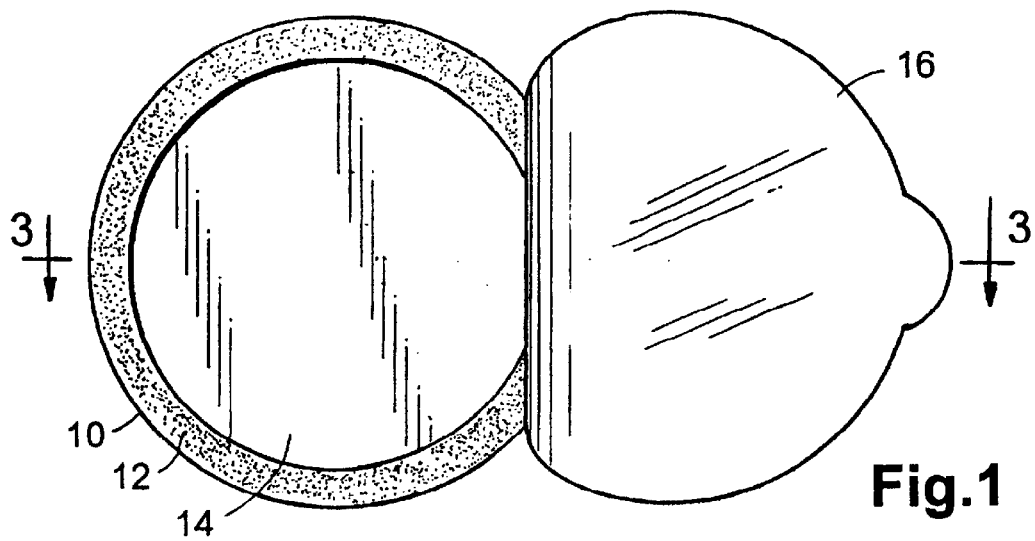
FIG. 1 if a plan view of the preferred applicator.

The applicator of this invention is in the form of a saucer shaped disc and is preferably made of a soft, pliable, fine latex foam that is moisture proof. The disc has a raised peripheral edge with an adhesive top surface. Since its principal use is to apply medication to a bruise or a small area of the body, the preferred embodiment of the applicator is circular as illustrated in FIG. 1, but there may be instances when it is advantageous to use a rectangular or square applicator as shown in FIG. 2, or an irregular shaped applicator.

The circular applicator 10 for traumas to the hip, leg or torso areas is between two and eight inches in overall diameter including a short ½ inch wide circular border strip 12. The applicator 10 is approximately ¼ high overall including the border strip 12 which surrounds a center portion 14 of ⅛ inch in thickness. The fineness of the thin foam in the center portion 14 renders it nearly impervious to moisture. The top surface of the border strip 12 is coated with an adhesive which adheres to the skin of the patient, and when filled with medication 13, the applicator is sealed by covering the entire top of the applicator 10 with a thin Teflon® sheet 16 adhering it to the adhesive on the surface of the border strip 12. FIG. 1 shows the Teflon® sheet 16 partially removed from the top of the applicator.

Figure 2:
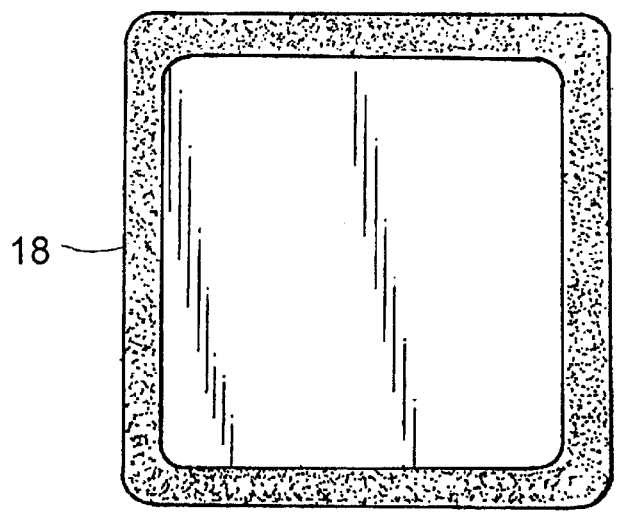
FIG. 2 is a plan view of an alternate applicator.
Figure 3:
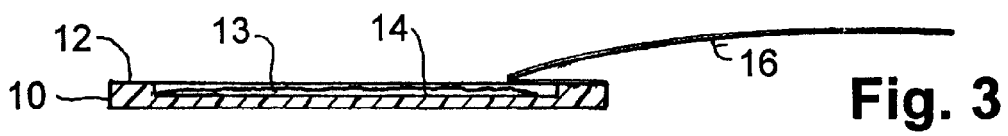
FIG. 3 is a sectional view along the lines 3—3 of FIG. 1

FIG. 2 is a plan view of a square embodiment of the applicator of FIG. 1. The square applicator 18 may be 2×2 for a wrist pad to 8×8 inches for a shoulder pad, and ¼ inches thick with ½ inch wide side strips 20 that have adhesive surfaces. The applicator 18 of FIG. 2 is identical to applicator 10 of FIG. 1, except for the shape.

Any salve or thick type of medication may be used with the applicators. Many people, especially those involved in heavy physical activities or contact sports, such as soccer or football, receive minor injuries to various parts of their bodies resulting in swelling, tenderness and discomfort to the area. If that injury is on a hand, arm, elbow or foot, it may be relieved with ease by soaking the area in a saturated solution of epsom salts in water. However, if the injury is in other parts of the body, soaking is difficult. However the full equivalent of the epsom salts soaking is achieved by replacing the water with glycerin, making a gel of only epsom salts and glycerin, spreading the gel over the high point of the swelling. A fully prepared manager or team doctor would have a supply of applicators filled with the epsom salts gel and sealed with the Teflon® seal. Then when an injury occurs he can ice the area for a few minutes and then peel off the Teflon® seal and apply the applicator over the swelling or most tender areas of the injured athlete.

The epsom salts gel healing pack should not be used over the facial area, bacterial or fungal infections, burns, abrasion or cuts of any size. The ingredients are water soluble, so the applicator should be removed during bathing and replaced later. The applicator should be replaced every 24 hours or until the swelling has reduced and the area has healed.

I claim:

1. An applicator for soaking various body parts with a gel medication, said applicator comprising:

a floor of a sheet of thin, pliable, moisture impervious, latex foam;

a wide border strip on said floor surrounding the periphery of said sheet, said border strip being formed of thin, pliable, latex foam having a top surface that is coated with an adhesive, the gel medication consisting of only epsom salts and glycerin and being applied on said floor within said border strip.

2. The applicator claimed in claim 1 further including a thin Teflon cover sheet for applying to said adhesive for sealing said gel medication.

3. A healing pack for providing the equivalent of an epsom salts and water soaking of sprained and swollen body parts, said healing pack comprising:

a circular floor of pliable, moisture impervious, foam sheet approximately ⅛ inch thick and between two and eight inches in diameter;

a border strip on said floor surrounding said floor, said strip approximately ⅛ inch high and ½ inch wide, said strip having a top surface coated with an adhesive; and a gel mixture consisting of only epsom salts and glycerin applied to said floor.

4. The healing pack claimed in claim 3 further including a thin Teflon covering applied to said adhesive for sealing said mixture of epsom salts and glycerin.

5. The healing pack claimed in claim 3 wherein said floor is rectangular in shape.

6. A method of applying an epsom salts soak to a body part inaccessible to normal soaking, said method comprising the steps of:

provinding an applicator of a pliable, moisture impervious, saucer shaped foam disc, said disc having a raised peripheral edge with an adhesive top surface;

mixing only epsom salts with glycerin to obtain a gel;

applying said gel inside the edge of said applicator;

adhering said applicator to the body part; and replacing the applicator every 24 hours or until the swelling has reduced and the area has healed.

* * * * *